(12) United States Patent
Merrill

(10) Patent No.: US 6,727,398 B2
(45) Date of Patent: Apr. 27, 2004

(54) METHODS AND SYSTEMS FOR PURIFYING STYRENE FEEDSTOCK COMPRISING USE OF LOW PALLADIUM CATALYST

(75) Inventor: James T. Merrill, Katy, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/850,672

(22) Filed: May 7, 2001

(65) Prior Publication Data

US 2002/0193651 A1 Dec. 19, 2002

(51) Int. Cl.[7] .................................................. C07C 7/10
(52) U.S. Cl. ..................... 585/833; 585/836; 585/877; 585/850; 585/856; 208/251 R; 208/253
(58) Field of Search ................................. 585/804, 841, 585/850, 259, 260, 258, 265, 266, 269

(56) References Cited

FOREIGN PATENT DOCUMENTS

EP          0584054 A1  *  2/1994

* cited by examiner

*Primary Examiner*—Walter D. Griffin
*Assistant Examiner*—Tam Nguyen
(74) *Attorney, Agent, or Firm*—Bradley A. Misley

(57) ABSTRACT

Apparatus, methods and systems useful for removing phenylacetylene from crude styrene feedstock are disclosed. Generally the processes and systems comprise the catalytic reduction of phenylacetylene to produce styrene via injection of a phenylacetylene reducing agent, such as hydrogen. A phenylacetylene reduction catalyst preferred herein comprises palladium on a calcium aluminate carrier, wherein the catalyst comprises less than 0.3 weight percent palladium.

8 Claims, 4 Drawing Sheets

METHODS AND SYSTEMS FOR PURIFYING STYRENE FEEDSTOCK COMPRISING USE OF LOW PALLADIUM CATALYST

BACKGROUND OF THE INVENTION

1. Field of the Invention

The present invention relates to purification and polymerization of monovinyl aromatic compounds. In another aspect, the present invention relates to purification and polymerization of styrene monomers. In even another aspect, the present invention relates to apparatus, systems and processes for removing contaminants from styrene monomer feedstock. In yet another aspect, the present invention relates to apparatus, systems and processes for reducing the amount of phenylacetylene in a styrene monomer feed, wherein the apparatus, systems and processes comprise a catalyst generally having less than 0.3 weight percent palladium.

2. Description of the Related Art

In the manufacture of monovinyl aromatic polymer compounds and more particularly in the manufacture of polystyrene, a first step comprises the reaction of benzene together with ethylene to form ethylbenzene. Ethylbenzene is dehydrogenated in an EB Dehydro unit to form styrene monomers. The resulting styrene monomers are then polymerized, usually in the presence of a polymerization initiator or catalyst, to form polystyrene resin.

If the ethylbenzene is dehydrogenated one step too far, an undesirable side product, phenylacetylene, is formed. As a result, the product stream from the Dehydro unit contains styrene, ethylbenzene, and trace amounts of phenylacetylene. The ethylbenzene can be easily removed by conventional processes, such as distillation, leaving styrene monomer and phenylacetylene. However, removal of phenylacetylene is much more difficult and distillation does not suffice.

The presence of phenylacetylene in the styrene monomer feedstock has undesirable consequences on the polymerization process. In a free-radical polymerization process, the presence of phenylacetylene has detrimental effects on chain length and polymerization rate because it is a poor chain transfer agent. In an anionic polymerization process, phenylacetylene consumes a stoichiometric amount of the catalyst, such as, for example, butyllithium, wherein one molecule of butyllithium is removed from the polymerization process by each molecule of phenylacetylene. This loss of catalyst can lead not only to high costs, but also to difficulty in controlling the molecular weight of the polymerized product, an increase in the concentration of low molecular weight polymer, and the presence of unreacted styrene in the polystyrene. Residual styrene monomer, which is a suspected carcinogen, contributes to off-taste, odor, off-color and other degradation of the polystyrene.

Clearly, the presence of phenylacetylene in a styrene monomer feedstock has adverse effects on cost of polymerization, control of the polymerization process, and the quality of the resulting polystyrene.

Catalytic attempts to decrease the level of phenylacetylene in styrene monomer streams have involved the injection of high levels of hydrogen gas into the stream. The phenylacetylene is then reduced to styrene. Unfortunately, any hydrogen present in stoichiometric excess of the phenylacetylene also results in a significant conversion of styrene back to ethylbenzene, thus causing a lower styrene concentration and a lower conversion rate.

U.S. Pat. No. 5,156,816, issued to Butler et al., discloses a system for purifying styrene monomer feedstock using ethylbenzene dehydrogenation waste gas. The system comprises a palladium catalyst on a theta-alumina carrier wherein the catalyst contains 0.3 weight percent palladium.

In spite of advancements in the art, many PAR systems and methods are inefficient and suffer from catalyst failure due to plugging or attrition of the catalyst. Methods and systems for purifying monovinyl aromatic feedstock that do not suffer from the limitations of the prior art have not been described.

Thus, there is a need in the art for methods of efficiently removing phenylacetylene contaminant from aromatic polyvinyl feedstock, said methods utilizing a catalyst that does not fail due to attrition, fluidization, or other loss of activity.

There is another need in the art for a system of efficient phenylacetylene removal from aromatic polyvinyl feedstock.

These and other needs in the art will become apparent to those of skill in the art upon review of this specification, including its drawings and claims.

SUMMARY OF THE INVENTION

It is an object of the present invention to provide methods of efficiently removing a phenylacetylene contaminant from aromatic polyvinyl feedstock wherein the methods comprise a catalyst that does not fail due to attrition or fluidization or other loss of activity.

It is another object of the present invention to provide a system useful for efficient removal of phenylacetylene from aromatic polyvinyl feedstock.

Thus, one embodiment of the present invention is directed to methods of purifying crude styrene monomer feedstock. The methods comprise use of a low palladium catalyst having less than 0.3 weight percent palladium.

Another embodiment of the present invention is directed to a system of purifying a crude styrene monomer feedstock. The systems of the invention comprise reducing the phenylacetylene levels of monovinyl aromatic monomer feedstock in polymerization systems by the use of either a two-bed reactor, or a pair of catalyst reactors. Each bed or reactor has injection means for injecting a phenylacetylene reducing agent, such as hydrogen gas, into the monomer reaction stream to reduce phenylacetylene into styrene. Generally the catalyst reactors comprise a low palladium catalyst having less than 0.3 weight percent palladium, preferably less than about 0.1 weight percent palladium.

DETAILED DESCRIPTION OF THE INVENTION

Figure 1:
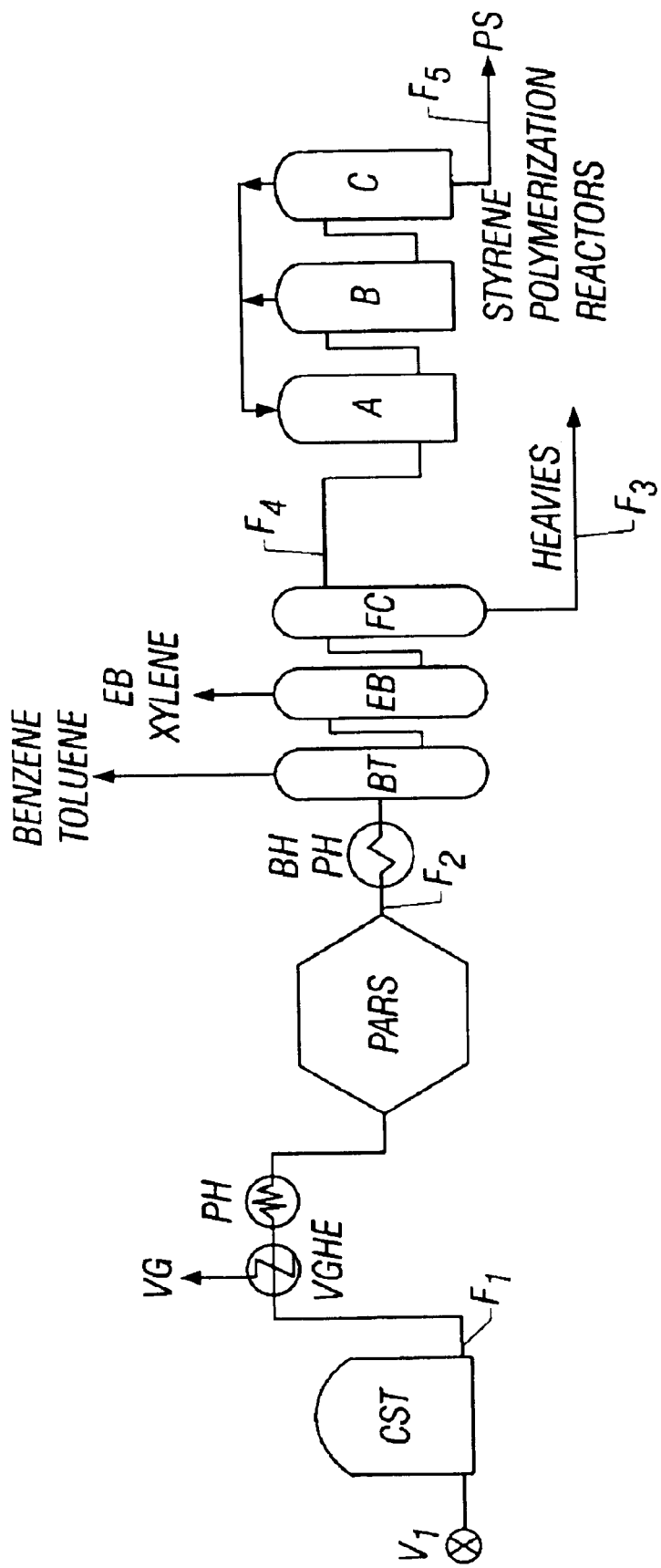
FIG. 1 is a schematic representation of a conventional PAR system.

One embodiment of the present invention is directed to a process for purifying crude styrene. Preferably the crude styrene is a styrene monomer feedstock created by the dehydrogenation of ethylbenzene (EB). The purification process comprises decreasing the level of phenylacetylene (PA) contaminate in the styrene monomer feedstock by the addition of a phenylacetylene reducing agent which reduces phenylacetylene to styrene. Preferably the reducing agent is hydrogen. The processes of the invention comprise subjecting crude styrene containing phenylacetylene contaminant to heat and raising the temperature of the styrene to about 150° F. The heated crude styrene, containing high levels of phenylacetylene, is then subjected to a phenylacetylene reduction process by reacting hydrogen with the phenylacetylene in at least two separate catalyst beds, wherein each bed comprises catalyst having an extremely low level of palladium (Pd).

Catalysts useful in the present invention generally contain from about 0.01 to less than 0.3 weight percent palladium, preferably from about 0.02 to about 0.2 weight percent palladium, and more preferably from about 0.03 to about 0.1 weight percent palladium. In a particularly preferred embodiment, the catalyst of the invention has about 0.03 to less than about 0.05 weight percent palladium.

In addition, the catalysts utilized in the present invention are dispersed on a calcium aluminate carrier and generally have a density greater than 50 lbs/ft$^3$, preferably greater than about 55 lbs/ft$^3$, more preferably greater than about 60 lbs/ft$^3$, and most preferably greater than about 62 lbs/ft$^3$. In a particularly preferred embodiment, the catalyst of the invention has a density of about 66 lbs/ft$^3$.

The catalysts used herein do not suffer from catalyst loss resulting from attrition by fluidization. Thus, the catalysts utilized herein will not fluidize in the processes and systems of the invention. Generally the catalyst used in the present invention has a minimum fluidization velocity of greater than about 0.05 feet/second, preferably greater than about 0.1 feet/second, and a process velocity of a value less than that of the fluidization velocity. A particularly preferred minimum fluidization velocity is about 0.125 feet/second, and a particularly preferred process velocity is about 0.114 feet/second.

An example of a catalyst found to be particularly useful in the present invention is Catalyst 38-6 by Synetix. Catalyst 38-6 is a selective hydrogenation catalyst dispersed on a ceramic support made of calcium aluminate, and has about 0.03 to 0.04 weight percent palladium (about 300 ppm to about 400 ppm palladium), a density of about 66 lbs/ft$^3$, a minimum fluidization velocity of about 0.125 ft/s, and a process velocity of about 0.114 ft/s. Catalyst 38-6 is available in the form of cylindrical pellets having a diameter of about 3.4 mm and a length of about 3.2 mm to about 3.7 mm, and a mean vertical crush strength of greater than about 50 kgf.

Other known hydrogenation catalysts might also be successfully utilized in the present invention. Of particular interest are the metals of Groups VIIB and VIII, the transition metals, including platinum, nickel, iridium, ruthenium, rhodium, osmium, and rhenium. Other possibilities include the aforementioned transition metals modified with Group IB and IIB metals such as gold, copper, and zinc. Other catalyst geometries may also be utilized herein, for example, extruded spherical pellets rather than cylindrical ones. In addition to calcium aluminate carriers, other known carriers might be utilized, such as silica, and sodium alumina silicates. Most preferably, the catalyst utilized herein is Synetix's Catalyst 38-6.

In the processes and systems of the present invention, phenylacetylene is reduced into styrene by addition of a phenylacetylene reducing agent, preferably hydrogen. The processes and systems of the present invention comprise the use of at least one of the following sources of hydrogen: 1) pure hydrogen; 2) hydrogen provided by the vent gas from the EB Dehydro unit (advantageous because of its ready availability); 3) hydrogen mixed with a diluent; and 4) hydrogen and a catalyst modifier such as carbon monoxide (CO), wherein the CO acts as a catalyst modifier to decrease the selectivity of the catalyst from reduction of styrene, and to increase its selectivity toward the reduction of phenylacetylene. If the hydrogen is mixed with a diluent, one particularly advantageous diluent is nitrogen, generally at a ratio of $N_2$ to $H_2$ in the range of about 1:2 to about 4:1. Although the diluent preferred herein is nitrogen, other diluents, such as fuel gas, may also be used with the present inventive process. If carbon monoxide is used as a catalyst modifier, the levels of carbon monoxide are generally about 1000 to about 2000 ppm, preferably about 1700 ppm.

In addition to the reduction of phenylacetylene by means of pure hydrogen, an inert diluent may be utilized to control the reaction of styrene and hydrogen in the reactors to the point that very little styrene reduction and a high level of phenylacetylene reduction are achieved. One source of hydrogen which can be used involves vent gas from the EB dehydrogenation process which has been already used in a heat exchanger of the system to preheat the crude styrene monomer prior to reaction in the first catalyst bed. The vent gas hydrogen can be combined with a pure diluent such as nitrogen gas supplied by means such as a nitrogen gas pipeline, railroad or truck tank care; or even bottled nitrogen gas. A typical EB dehydro vent gas analysis reveals the vent gas comprises about 89% hydrogen, about 7% carbon dioxide, less than 1% carbon monoxide, and the remainder being mostly hydrocarbons such as methane.

Referring now to FIG. 1, there is provided a highly simplified schematic flow diagram representing a conventional styrene purification and polymerization process. One possible placement of a phenylacetylene reduction system of the present invention is indicated therein by the PAR hexagon.

In FIG. 1, styrene monomer which has been created from the dehydrogenation of ethylbenzene is provided at valve V1 from where it flows into the crude styrene storage tank CST. Crude styrene flows from the storage tank CST via flow line F1 into a vent gas heat exchanger VGHE in order to raise the temperature of the styrene, and from there into an optional preheater PH. From the preheater the crude styrene passes into the phenylacetylene reduction system PARS where the phenylacetylene in the crude styrene is reduced to acceptable levels. From the PARS, the refined crude styrene then flows through flow line F2 into the BT Column Preheater BTPH where the styrene temperature is raised prior to being injected into the BT Column. In this column, benzene and toluene are distilled off and removed through the top. The refined styrene then passes into the EB Column where ethylbenzene and xylene are removed.

The EB Column has a second output that contains the "heavies" and the refined styrene monomer. These are flowed into the Finishing Column FC where the heavies are separated from the purified styrene. The heavies are removed out flow line F3 and the purified styrene flows through line F4 into the styrene polymerization reactors A, B and C. The heavies removed from the finishing column comprise pre-polymerized polystyrene, indene, indane, and other heavies referred to as "tars".

The styrene monomer is next polymerized in the three reactor polymerization system ABC and finished polystyrene is removed as indicated at PS through flow line F5. Columns B and C are shown having recycle lines exiting the top of the columns to recycle unpolymerized styrene monomer back into column A.

Figure 2:
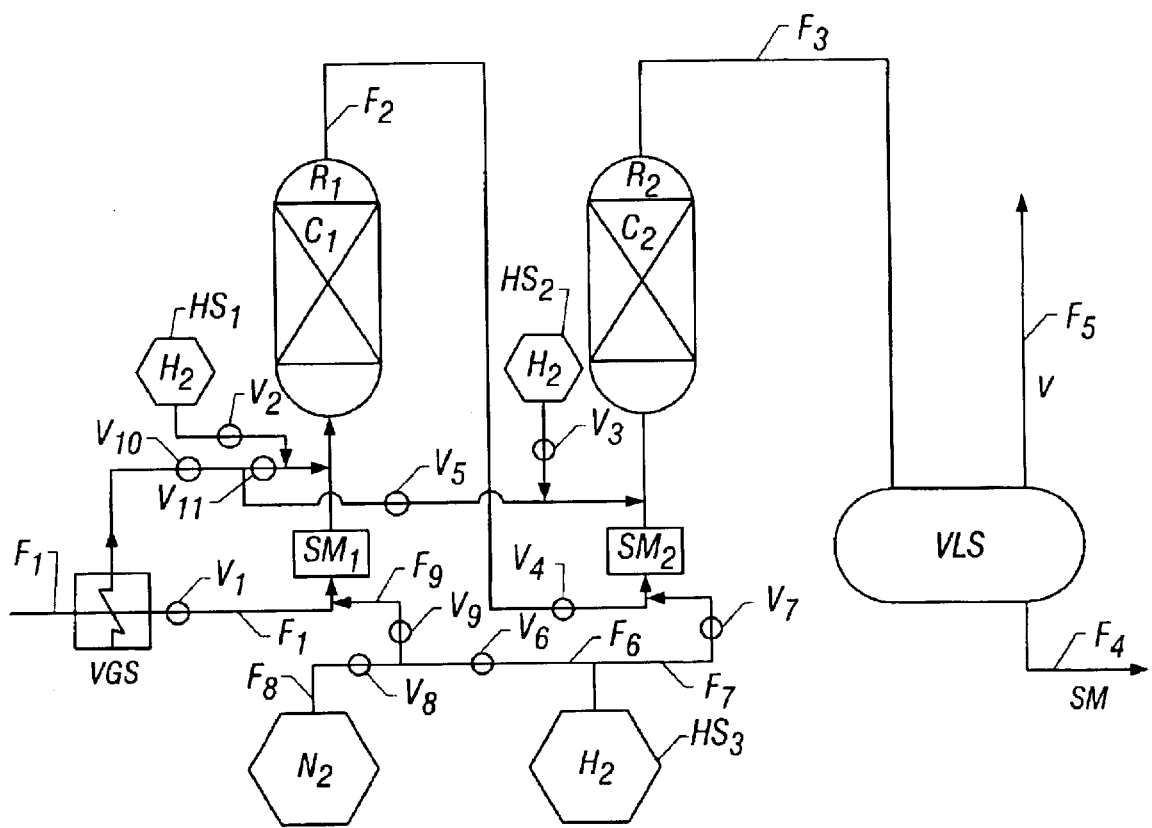
FIG. 2 is a schematic representation of one embodiment of a PAR system of the invention.

Referring now to FIG. 2, there is provided a schematic representation of several embodiments of a PAR system of the present invention. A first embodiment involves the injection of pure hydrogen into crude styrene feedstock prior to the styrene entering reactor vessels, such as R1 and R2. The pure hydrogen may be injected either before the crude styrene passes through a static mixer, after the crude styrene passes through a static mixer, or both. Another embodiment involves the injection of hydrogen and nitrogen as opposed to pure hydrogen. The manipulation of valves V1 through V11, allows for the injection of either pure hydrogen, hydrogen and nitrogen, or any combination thereof, into the PAR process at the aforementioned points.

In FIG. 2, crude styrene flow line F1 leading from the crude styrene tank CST flows through the vent gas styrene heat exchanger VGS and is controlled by means of flow control valve V1 in line F1. The flow of crude styrene through vent gas styrene heat exchanger VGS serves at least two purposes. First, the exchanger brings the crude styrene crude up to a temperature of generally about 150° F. which is sufficient to initiate the phenylacetylene reduction process. A second purpose is to provide an optional vent gas supply which serves as a possible hydrogen source for hydrogen injection into reactor R1 and reactor R2 via control valves V10, V11 and V5.

The crude styrene is passed from vent gas styrene heat exchanger VGS through valve V1, flows up through static mixer SM1 and into first reactor vessel R1 containing catalyst bed C1. The crude styrene flows upward through catalyst bed C1 and exits through flow line F2 and is passed through valve V4 into second static mixer SM2, and then flows into second reactor R2 containing second catalyst bed C2.

Reactor vessels R1 and R2 may be any type of vessel known in the art but are preferably liquid-full, upflow catalyst reactors. Catalyst beds C1 and C2 may be of any type known in the art, such as a fixed bed, and preferably contain a cylindrical catalyst. Generally the catalyst is on a calcium aluminate carrier and is made up of less than 0.3 weight percent palladium, preferably less than 0.1 weight percent palladium, and more preferably less than 0.05 weight percent palladium. In a particularly preferred embodiment, catalyst beds C1 and C2 comprise a cylindrical catalyst on a calcium aluminate carrier, wherein the catalyst comprises about 0.03 weight percent palladium.

Pure hydrogen from hydrogen sources HS1 and HS2 are provided for each reactor R1 and R2, respectively, and are controlled by valves V2 and V3, respectively. Although HS1 and HS2 are shown as separate hydrogen supply source, HS1 and HS2 may be from the same single hydrogen source such as, for example, a hydrogen supply pipeline, railroad or truck tank cars of hydrogen, or even bottled hydrogen.

From reactor R2, the purified styrene monomer stream flows via flow line F3 to vapor liquid separator vessel VLS from which the purified styrene monomer stream SM exits via flow line F4. The separated vapors V exit vapor liquid separator vessel VLS through flow line F5 to be recycled in the process at the appropriate points.

A third pure hydrogen source, HS3, may also be used to provide hydrogen to the system. Hydrogen from hydrogen source HS3 may be supplied via flow lines F6 and F9 via valves V6 and V9, respectively, to the crude styrene flow coming from the vent gas styrene heat exchanger VGS before the styrene flow enters static mixer SM1. Hydrogen from hydrogen source HS3 may also be supplied to the styrene flow via flow line F7 through valve V7 after the flow has exited reactor R1 but before it has passed through static mixer SM2.

Yet another source of hydrogen which can be used in the present invention is vent gas from the EB dehydrogenation process. Analysis of a typical EB dehydro vent gas shows the contents therein to be about 89% hydrogen, about 7% carbon dioxide, less than 1% carbon monoxide, and the remainder mostly hydrocarbons such as methane. Generally the vent gas has been passed through vent gas heat exchanger VGS together with the crude styrene at the time of preheating the crude styrene monomer. The vent gas hydrogen can be combined with a pure diluent, such as nitrogen gas supplied a nitrogen gas pipeline, railroad or truck tank care; or even bottled nitrogen gas.

An inert diluent may be utilized to control the reaction of styrene and hydrogen in the reactors to the point that very little styrene reduction and a high level of phenylacetylene reduction are achieved. A preferred diluent is nitrogen. The nitrogen may be added to the hydrogen coming from hydrogen source HS3 at either one or both of the sites at which hydrogen from H3 is added. The ratio of $N_2$ to $H_2$ should be in the range of from 1:2 to 4:1, preferably about 1:1, diluent to hydrogen.

If nitrogen is used herein as a diluent, it may be provided by nitrogen source N2. The nitrogen gas from source N2 flows through flow line F8 controlled by valve V8. The nitrogen may then be combined with the hydrogen from source H3, and the combination injected into flow line F9 via valve V9, at which point it is added to the crude styrene coming from vent gas heat exchanger VGS. The nitrogen, hydrogen and crude styrene are then mixed in static mixer SM1 to provide a thorough mixing of the gases and the crude styrene feedstock before entering reactor R1. A combination of nitrogen and hydrogen may also be supplied to the styrene flow via flow line F7 via valve V7 prior to the styrene flow entering static mixer SM2. The mixture of hydrogen and nitrogen is injected into the styrene flow and subjected to the action of static mixer SM2 to provide a thorough mixing of the gases and the crude styrene feedstock before entering reactor R2. Preferably, a diluent gas such as nitrogen is utilized only in the first reactor bed R1, but may be utilized in both reactors R1 and R2 if desired.

Alternatively, instead of mixing the hydrogen with a diluent gas, the hydrogen may be mixed with a catalyst modifier such as, for example, carbon monoxide (CO). Generally the CO is supplied to the PAR system in the EB dehydro vent gas in amounts of up to less than about 1%, and preferably around 0.01 up to about 0.2%, but may also be supplied by an independent source and mixed with pure hydrogen. The synergistic manner in which the carbon monoxide and hydrogen interact in the present invention is unexpected because CO normally acts as a "poison" to precious-metal catalysts. Surprisingly, however, in the present invention the CO does not poison the catalyst but may provide selectivity of hydrogenation of towards phenylacetylene and away from styrene. Although not wishing to be limited or bound by theory, it is possible that the CO does not permanently bond to the catalyst surface but instead, blocks those activation sites selective toward styrene while leaving available those sites active toward phenylacetylene. The change may involve changing the electronic configuration of the surface of the metal or the electronic environment thereon.

Thus the present invention involves the use of either pure hydrogen as a reducing agent, hydrogen provided by means of EB vent gas, hydrogen mixed with a nitrogen diluent, or the use of hydrogen and carbon monoxide wherein the CO acts as a catalyst modifier to decrease the selectivity of the catalyst from reduction of styrene and to increase its selectivity toward the reduction of phenylacetylene. Preferably the hydrogen source of HS1 and HS2 is vent gas.

The initial level of phenylacetylene in crude styrene is in the amount of up to about 250 parts per million (ppm). After reaction in the PAR processes and systems of the present invention, the level of phenylacetylene in the crude styrene feedstock is preferably less than about 10 parts per million.

Referring still to FIG. 2, the purified styrene monomer is then flowed through flow line F3 to the vapor liquid separator VLS where the diluent gas and any possible remaining hydrogen gas (designated F5) are separated through vapor line V. The crude styrene feedstock comprising about 61% styrene and 39% ethylbenzene (designated SM) are flowed from vapor liquid separator VLS through styrene monomer line F4. From here styrene monomer line F4 may connect with a benzene/toluene column, such as column BT indicated in FIG. 1, where traces of benzene and toluene are separated from the feedstock. Ethylbenzene is then removed from the styrene in an ethylbenzene column located downstream of the benzene/toluene column, such as column EB in FIG. 1, and the final refining step of the styrene monomer is accomplished in a finishing column, designated FC in FIG. 1.

Figure 3:
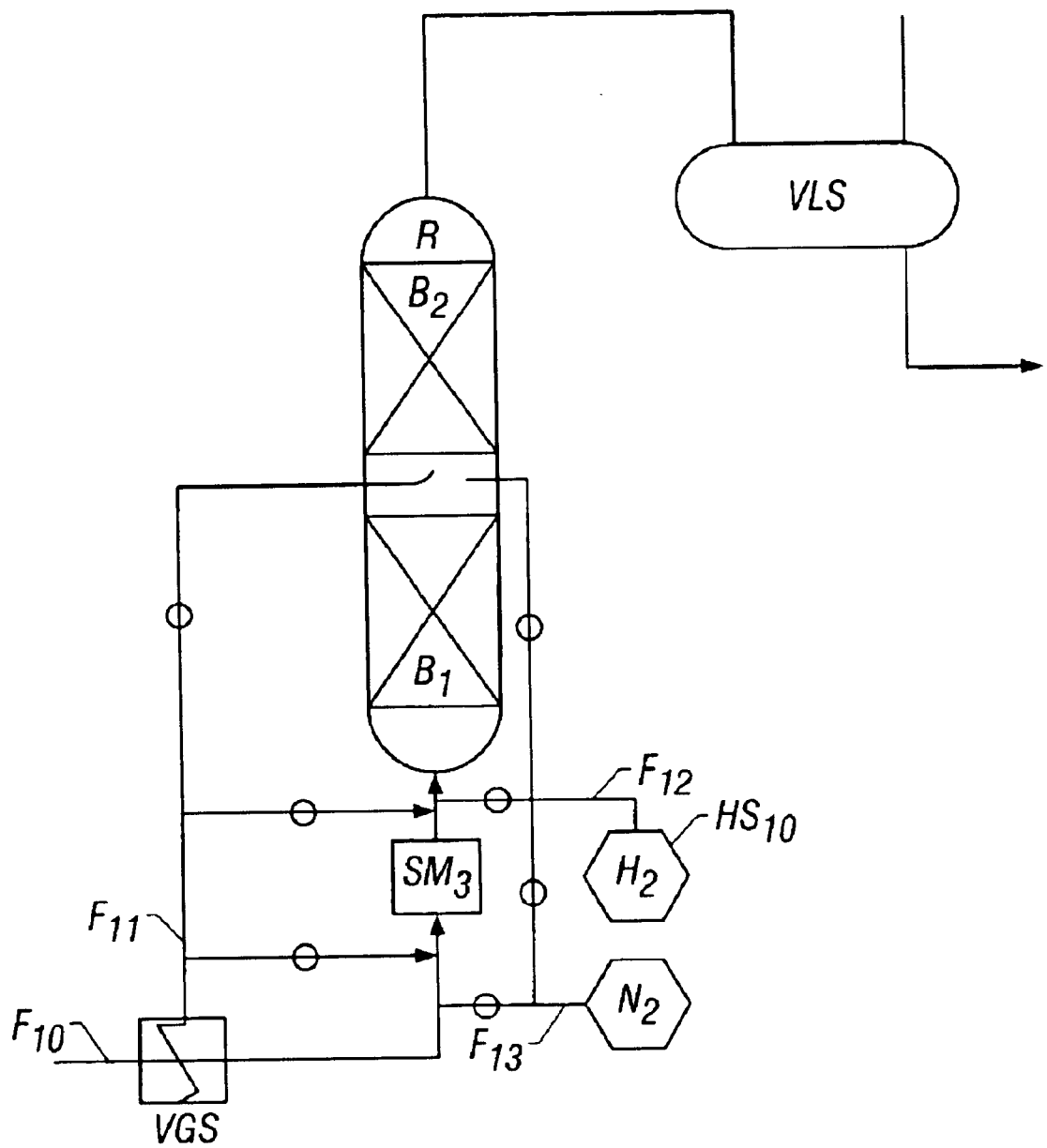
FIG. 3 is a schematic representation of another embodiment of a PAR system of the invention.

Referring now to FIG. 3, there is provided yet another embodiment of the present invention. In this embodiment, the two reactors R1 and R2 of FIG. 2 have been replaced with a single two-bed reactor having catalyst beds B1 and B2 comprising cylindrical catalyst of a calcium aluminate carrier with a palladium metal having preferably less than 0.3 weight percent palladium. A particularly preferred catalyst is Synetix's Catalyst 38-6 In the embodiment provided in FIG. 3, crude styrene enters through flow line F10 passing through vent gas styrene heat exchanger VGS and into static mixer designated SM3. From there the styrene flows into the reactor R passing first through catalyst bed B1 and then through catalyst bed B2. Vent gas from vent gas heat exchanger VGS is provided via flow line F11 through various valve means into three points in the PAR system, one point being prior to static mixer SM3, the second point being downstream of static mixer SM3 and the third point being in the central area of the reactor R between catalyst beds B1 and B2.

Hydrogen from hydrogen source HS10 may be supplied by flow line F12 and, as discussed above for the various hydrogen sources of FIG. 2, may be mixed with either carbon monoxide from a CO source, or with nitrogen from nitrogen source N2 through flow line F13 or it may be injected directly into the reactor either upstream or downstream of static mixer SM3, or in the central area of reactor R, by manipulation of the various valves in the various flow lines.

The present invention prevents the reduction of styrene and phenylacetylene to ethylbenzene, and involves the use of multiple injection points, either by utilization of two reactors or of a two-bed single reactor. As disclosed herein, embodiments of the present invention utilize diluents, such as nitrogen, to slow the contact of hydrogen with the styrene monomer stream constituents. Other embodiments use a hydrogen gas combined with a catalyst modifier such as carbon monoxide to increase the selectivity toward phenylacetylene reduction.

The apparatus, processes, and systems of the present invention are successful in reducing phenylacetylene levels in styrene monomer streams from an undesirable level of up to 250 parts per million down to highly desirable levels of less than about 10 parts per million. Although not intending or wishing to be bound by theory, it is possible that the reason for such a high success ratio with the present invention is due to a combination of the chemistry involved as well as the geometry of the catalyst which allows the hydrogen and the phenylacetylene to come together to react.

The present invention also reduces the energy required to initiate the phenylacetylene reduction process. By use of the present invention, initializing the phenylacetylene reduction process can primarily be accomplished by use of the inherent heat content of the styrene feed at 150° F. from the VGS heat exchanger.

Generally the reactor pressure is operated at about 45 to about 90 psi inlet pressure, preferably about 50 to about 85 psi, more preferably about 60 to about 80 psi, and most preferably about 70 to about 75 psi. In the case of a two-reactor system, with an initial phenylacetylene concentration of about 200 ppm, a hydrogen to phenylacetylene ratio of about 16 to 1 is split equally between each reactor. Likewise, in the two-bed reactor system with the dual injection locations, a 16 to 1 ratio of hydrogen to phenylacetylene is split equally between the two points. Although other ratios of hydrogen to phenylacetylene may be utilized herein, a 16 to 1 ratio provides optimal phenylacetylene reduction and low conversion of styrene back to ethylbenzene.

A desirable flow rate through the reactor system for the present invention is in the range of about 10 to up to 240 LHSV. Although an LHSV in the range up to 240 will work in the present invention, the preferred LHSV rates are in the range of about 20 to about 120, because the higher rates are believed to contribute to shorter catalyst life. Preferably the overall LHSV rate is about 60, more preferably about 30.

Generally the amount of styrene reduction, which is undesirable, by use of the present invention is a very low level of about 0.1% to 0.2% of the styrene being processed. Because ethylbenzene is removed from the styrene monomer and recycled back into the dehydrogenation process to be converted back into styrene, the conversion of styrene to ethylbenzene is not as detrimental to the process as is the presence of phenylacetylene. The 0.1% to 0.2% loss of styrene through reduction to ethylbenzene is negligible and very acceptable. By the use of the multi-bed reactor, lessor amounts of hydrogen can be used such that the lose of styrene through reduction drops to less than about 0.1% and phenylacetylene can be reduced to less than 30 parts per million, preferably less than about 10 parts per million.

All references cited herein, including research articles, all U.S. and foreign patents and patent applications, are specifically and entirely incorporated herein by reference.

EXAMPLES

The invention having been generally described, the following examples are provided merely to illustrate certain embodiments of the invention. It is understood that the examples are not intended to limit the specification or the claims in any manner.

Example 1
Phenylacetylene Removal Activity of the Present Invention

The objective of this experiment was to compare the phenylacetylene removal (PAR) performance of the present invention comprising the Synetix Catalyst 38-6 (triangles) to that of a conventional PAR method comprising the Criterion 05PAS#2 catalyst (circles). The Synetix Catalyst 38-6 has about 0.03 to about 0.04 weight percent palladium, is on a calcium aluminate carrier and has a catalyst bulk density of about 66 lbs/ft$^3$. The Criterion 05PAS#2 catalyst has 0.3 weight percent palladium, is on a theta-alumina carrier, and has a catalyst bulk density of 50 lbs/ft$^3$.

The experimental parameters were as follows:
RX3 in the recycle mode

| Mode | Upflow |
|---|---|
| Pressure | 125 psig |
| LHSV | 60 hr-1 |
| Catalyst Volume | 20 ml as whole extrudates |
| Reactor | 1" O.D., 9\16" I.D., 1\4" Thermowell |
| Hydrogen Rate | 16\1 Molar H---2\PA, 13 sccm |
| Recycle Rate | 17 ml/min |
| Fresh Feed (FF) | 60:40 Styrene:EB, TBC Free |
| FF Rate | 0.91 g/min (1.00 ml/min) |
| FF Composition | 0.4 wt % PA (for 200 ppm PA in total Reactor Feed) |
| Additive | None |
| Temperature | 150° F. (65.5° C.) |

Figure 4:
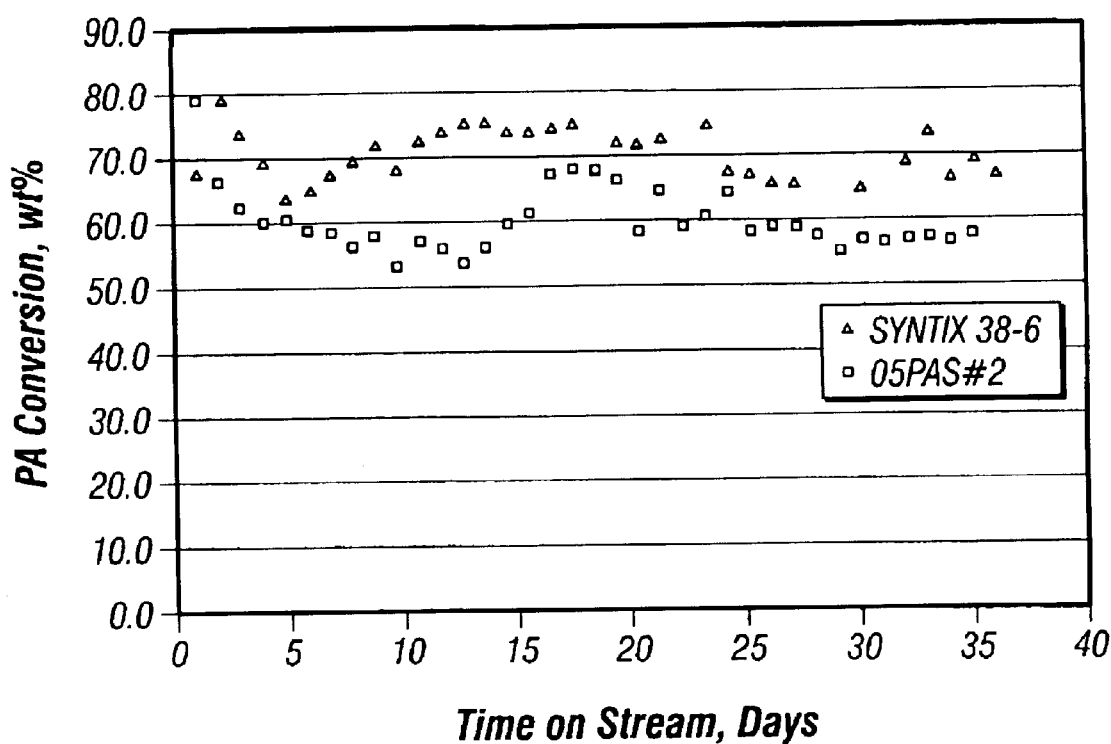
FIG. 4 illustrates the phenylacetylene removal activities of a system of the invention and a conventional system.

FIG. 4 provides graphic representation of the outcome of the study. As can be seen in FIG. 4, the present invention comprising Synetix Catalyst 38-6 outperforms a conventional method comprising Criterion 05PAS#2 catalyst.

Example 2

Water Excursion Test

The objective of this test was to expose the Synetix Catalyst 38-6 to free water under reaction conditions to determine if catalyst activity is lost. Water is a co-feed to the dehydrogenation process and, although the water is decanted upstream of the PAR reactor, it is possible that plant upsets could cause contact between the catalyst and water.

The experiment was performed under the same conditions used in Example 1. The process was performed until catalyst activity was stabilized. Water was then injected and the fresh feed rate was stopped. Upon observing free water in the effluent, water injection was stopped and normal fresh feed was resumed. It took several days to clear all water from the system.

Figure 5:
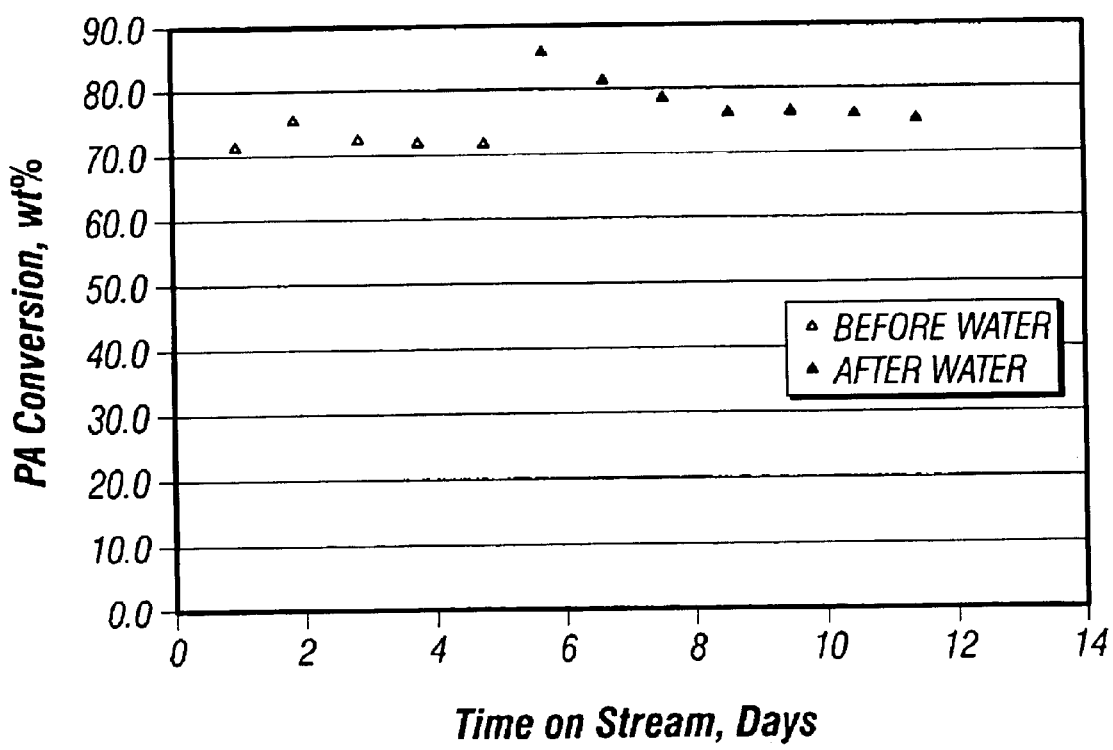
FIG. 5 illustrates the phenylacetylene removal activity of a system of the invention before and after a water excursion.

FIG. 5 provides graphic representation of the outcome of this study. As shown in FIG. 5 the PAR activity of the present invention comprising Synetix's Catalyst 38-6 is not lost after a water excursion.

A sample of Synetix Catalyst 38-6 was also soaked in water for three days. (The support material of Catalyst 38-6 is calcium aluminate, a material used for concrete cement.) Both the dry Catalyst 38-6 material and the water-saturated Catalyst 38-6 material had crush strengths that exceeded the capability of the catalyst crush strength tester which has a capacity of 20 lbs.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

I claim:

1. A method for decreasing the level of a contaminant in a crude styrene feedstock, the method comprising the steps of:

a) admixing a portion of a first reducing agent together with a first portion of crude styrene to produce a stream A, wherein said crude styrene comprises an initial level of a phenylacetylene;

b) contacting stream A with a first catalyst bed comprising a first catalyst comprising from about 0.01 to less than about 0.2 weight percent palladium to produce stream B, wherein stream B comprises a level of phenylacetylene less than the initial level of phenylacetylene.

2. The method of claim 1 further comprising the steps of:

c) admixing a portion of a second reducing agent together with stream B to produce stream C;

d) contacting stream C with a second catalyst bed comprising a second catalyst comprising from about 0.01 to less than about 0.2 weight percent palladium to produce stream D, wherein stream D comprises a level of phenylacetylene less than that of stream B.

3. The method of claim 2 wherein said first and second catalysts each comprise from about 0.03 to about 0.05 weight percent palladium.

4. The method of claim 2 wherein said first portion of crude styrene is a stream of styrene, wherein said crude styrene is produced by dehydrogenation of ethylbenzene in an ethylbenzene dehydrogenation unit, and wherein said first and second reducing agents are obtained as vent gas from said dehydrogenation unit.

5. The method of claim 3 wherein said first and second reducing agents comprise hydrogen gas.

6. The method of claim 4 wherein said first and second catalyst beds are in the same reactor unit.

7. The method of claim 4 wherein said first and second catalyst beds are each in a separate reactor unit.

8. The method of claim 3 wherein stream D comprises 60 to 97 percent less than the initial level of phenylacetylene in the crude styrene.

* * * * *